(12) United States Patent
Sixto et al.

(10) Patent No.: US 10,548,649 B2
(45) Date of Patent: Feb. 4, 2020

(54) CLAVICLE IMPLANTS

(71) Applicant: Biomet Manufacturing, LLC, Warsaw, IN (US)

(72) Inventors: Robert Sixto, Miami, FL (US); Andrea Suarez, Miami Springs, FL (US); Juergen A Kortenbach, Miami Springs, FL (US); Alejandro Perez, Miami, FL (US)

(73) Assignee: Biomet Manufacturing, LLC, Warsaw, IN (US)

( * ) Notice: Subject to any disclaimer, the term of this patent is extended or adjusted under 35 U.S.C. 154(b) by 201 days.

(21) Appl. No.: 15/136,398

(22) Filed: Apr. 22, 2016

(65) Prior Publication Data

US 2016/0310185 A1 Oct. 27, 2016

Related U.S. Application Data

(60) Provisional application No. 62/152,320, filed on Apr. 24, 2015.

(51) Int. Cl.
*A61B 17/80* (2006.01)
*A61B 17/88* (2006.01)

(52) U.S. Cl.
CPC ...... *A61B 17/8085* (2013.01); *A61B 17/8061* (2013.01); *A61B 17/8863* (2013.01)

(58) Field of Classification Search
CPC ............ A61B 17/8061; A61B 17/8076; A61B 2090/037
See application file for complete search history.

(56) References Cited

U.S. PATENT DOCUMENTS

| | | | | |
|---|---|---|---|---|
| 5,290,281 A | * | 3/1994 | Tschakaloff | A61B 17/8085 219/229 |
| 5,779,706 A | * | 7/1998 | Tschakaloff | A61B 17/8085 219/229 |
| 5,785,712 A | * | 7/1998 | Runciman | A61B 17/8085 606/283 |
| 6,716,234 B2 | | 4/2004 | Grafton et al. | |
| 7,632,277 B2 | | 12/2009 | Woll et al. | |
| 7,819,874 B2 | | 10/2010 | Woll | |

(Continued)

FOREIGN PATENT DOCUMENTS

CN 103505279 A 1/2014
JP 2011502574 A 1/2011

(Continued)

OTHER PUBLICATIONS

Fatah, Emam Elhak Abdel, "A Three-Dimensional Analysis of Bilateral Directional Asymmetry in the Human Clavicle", American Journal of Physical Anthropology 149, (2012), 547-559.

(Continued)

*Primary Examiner* — David W Bates
(74) *Attorney, Agent, or Firm* — Schwegman Lundberg & Woessner, P.A.

(57) ABSTRACT

A bone plate including a main bone plate body having two opposing curved sections adapted for a clavicle; a bendable waist portion narrower than the main body of the bone plate; and a node at each end of the main body connected to the main body by a bridge portion which is narrower than the main body, wherein the bridge includes a cut-out relief portion on a bottom side of the bone plate.

16 Claims, 10 Drawing Sheets

(56) References Cited

U.S. PATENT DOCUMENTS

| | | | |
|---|---|---|---|
| 7,892,256 B2 | 2/2011 | Grafton et al. | |
| 7,935,126 B2* | 5/2011 | Orbay | A61B 17/1728 606/101 |
| 8,133,225 B2 | 3/2012 | Pieske | |
| 8,282,674 B2 | 10/2012 | Gelfand | |
| 8,348,956 B2 | 1/2013 | Rabiner | |
| 8,425,513 B2 | 4/2013 | Frankle et al. | |
| 8,439,947 B2 | 5/2013 | Howard et al. | |
| 9,072,556 B2* | 7/2015 | Fritzinger | A61B 17/8057 |
| 9,144,443 B2* | 9/2015 | Leither | A61B 17/8057 |
| 9,757,172 B2* | 9/2017 | Andermahr | A61B 17/8061 |
| 9,814,504 B2* | 11/2017 | Ducharme | A61B 17/8061 |
| 2003/0006533 A1* | 1/2003 | Shikinami | A61B 17/8085 264/323 |
| 2007/0093835 A1 | 4/2007 | Orbay et al. | |
| 2007/0179531 A1 | 8/2007 | Thornes | |
| 2007/0185493 A1 | 8/2007 | Feibel et al. | |
| 2007/0225715 A1 | 9/2007 | Deffenbaugh et al. | |
| 2007/0270853 A1 | 11/2007 | Leung | |
| 2007/0293863 A1 | 12/2007 | Reimels et al. | |
| 2008/0077133 A1 | 3/2008 | Schulze | |
| 2008/0161861 A1 | 7/2008 | Huebner | |
| 2008/0221574 A1 | 9/2008 | Cavallazzi et al. | |
| 2008/0234676 A1 | 9/2008 | Schulze et al. | |
| 2008/0234679 A1 | 9/2008 | Sarin et al. | |
| 2009/0118768 A1 | 5/2009 | Sixto, Jr. et al. | |
| 2009/0281543 A1* | 11/2009 | Orbay | A61B 17/80 606/70 |
| 2009/0306724 A1* | 12/2009 | Leither | A61B 17/8057 606/289 |
| 2010/0131012 A1* | 5/2010 | Ralph | A61B 17/80 606/280 |
| 2012/0059424 A1* | 3/2012 | Epperly | A61B 17/8061 606/281 |
| 2013/0041375 A1 | 2/2013 | Fierlbeck et al. | |
| 2013/0172948 A1* | 7/2013 | Fritzinger | A61B 17/8057 606/86 R |
| 2017/0035478 A1 | 2/2017 | Andermahr et al. | |

FOREIGN PATENT DOCUMENTS

| | | |
|---|---|---|
| JP | 2013505071 A | 2/2013 |
| WO | WO-2016172536 A1 | 10/2016 |

OTHER PUBLICATIONS

Jiang, H., et al., "Operative treatment of clavicle midshaft fractures using a locking compression plate: Comparison between mini-invasive plate osteosynthesis (MIPPO) technique and conventional open reduction", Orthopaedics & Traumatology: Surgery & Research (2012) 98,, (2012), 666-671.

Schiffer, Gereon, et al., "Midclavicular Fracture: Not Just a Trivial Injury", Dtsch Arztebl Int 2010; 107(41): 711-7, (2010), 8 pgs.

Shimamura, Y., "Treatment of clavicle shaft fractures", vol. 32 No. 9—Partial English, (2013), 24-29.

"Minimally-invasive plate osteosynthesis (MIPO)", YThijmen, [Online]. [Accessed Oct. 30, 2017]. Retrieved from the Internet: <URL: https://youtu.be/oeF4IcL6Teo>, (Mar. 7, 2015), 4 minutes 3 seconds.

"International Application Serial No. PCT/US2016/028924 International Search Report dated Jul. 11, 2016", 7 pgs.

"International Application Serial No. PCT/US2016/028924 Written Opinion dated Jul. 11, 2016", 9 pgs.

"Canadian Application Serial No. 2,983,488, Office Action dated Oct. 31, 2018", 4 pgs.

"Japanese Application Serial No. 2017-555563, Office Action dated Oct. 23, 2018", (W/ English Translation), 5 pgs.

"Japanese Application Serial No. 2017-555563, Response filed Jan. 23, 2019 to Office Action dated Oct. 23, 2018", (W/ English Claims), 7 pgs.

"Canadian Application Serial No. 2,983,488, Examiner's Rule 30(2) Requisition dated Aug. 6, 2019", 3 pgs.

* cited by examiner

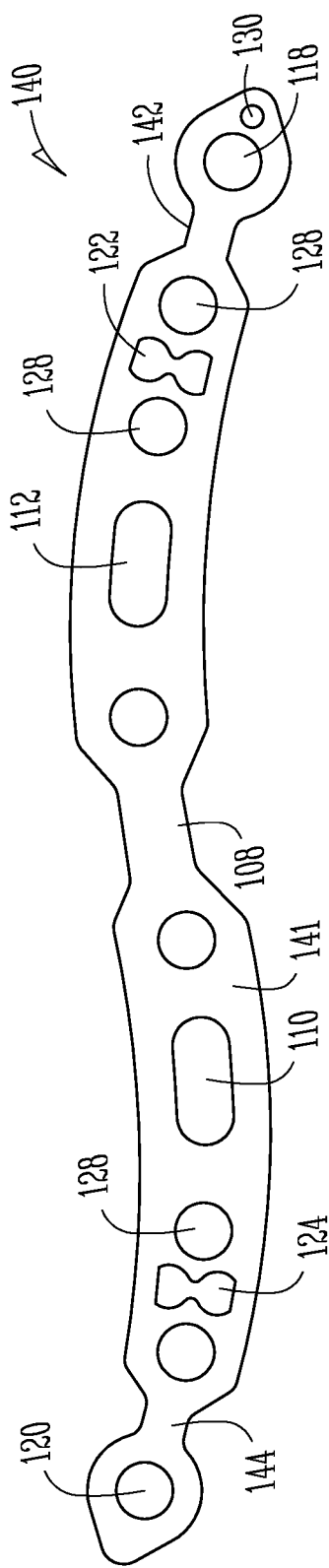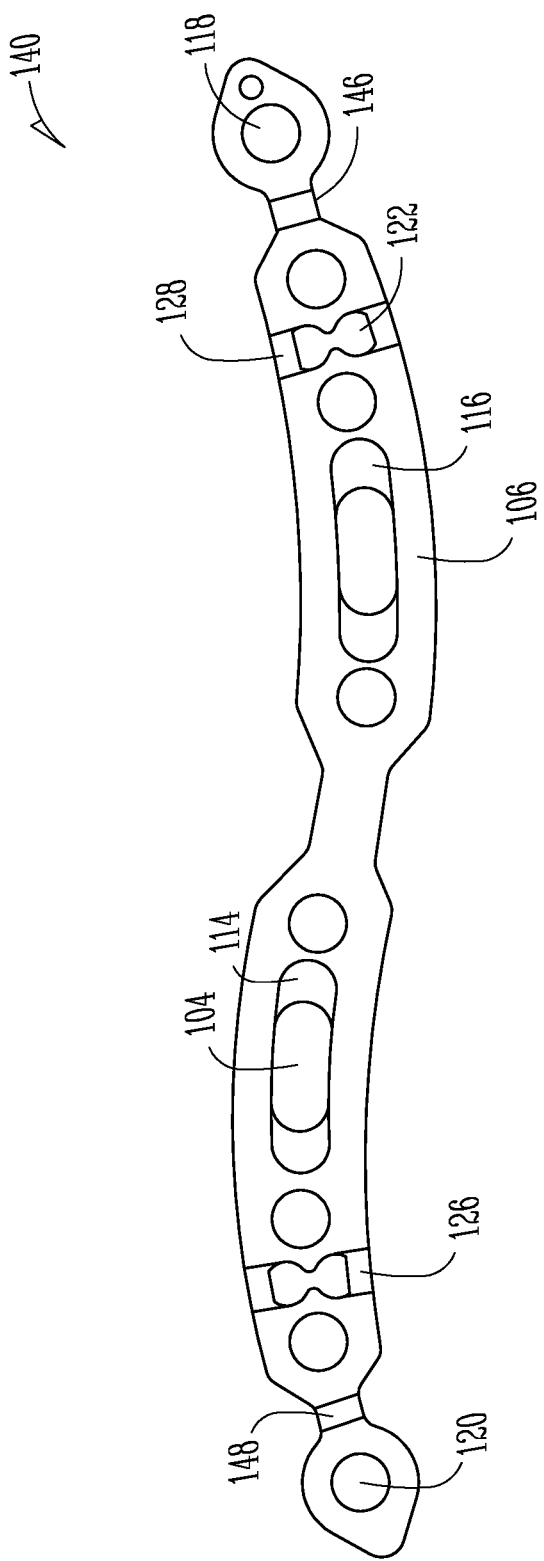

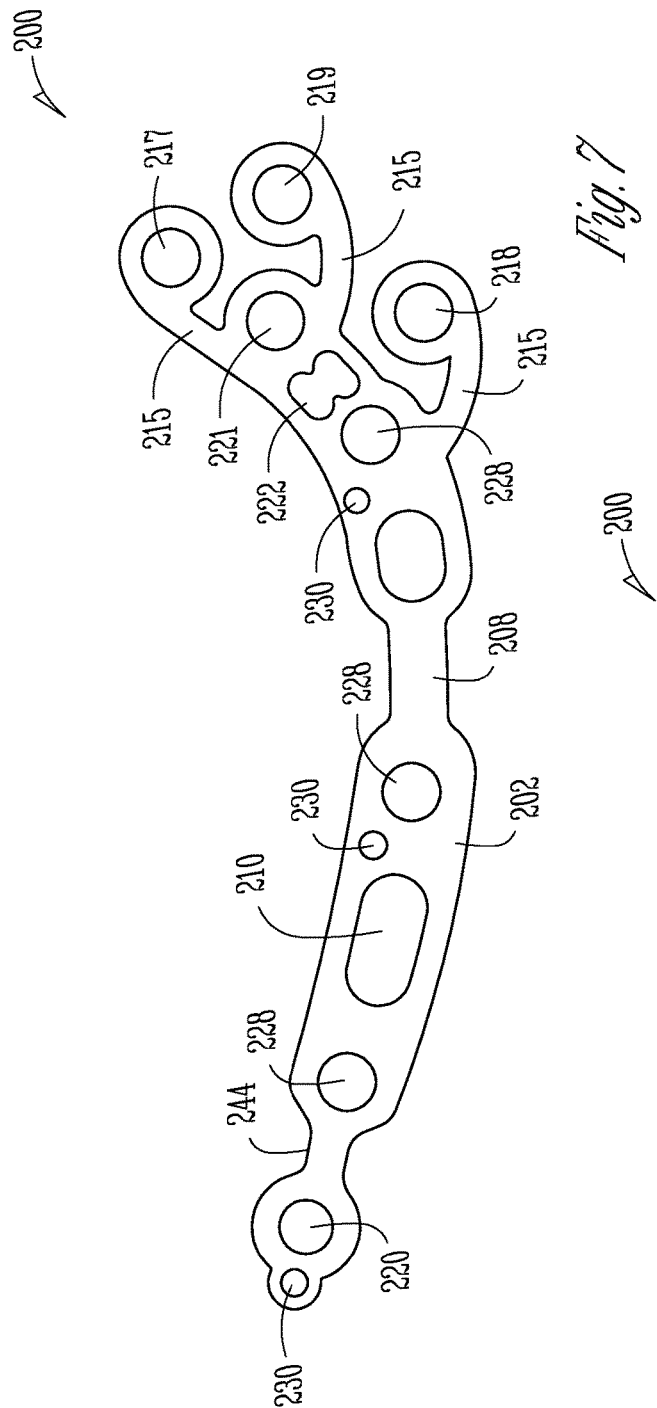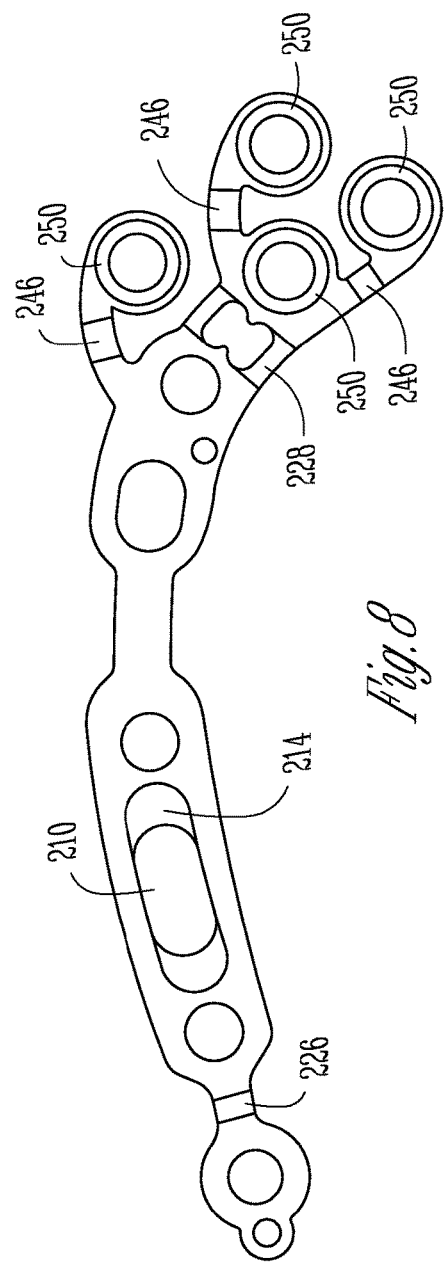

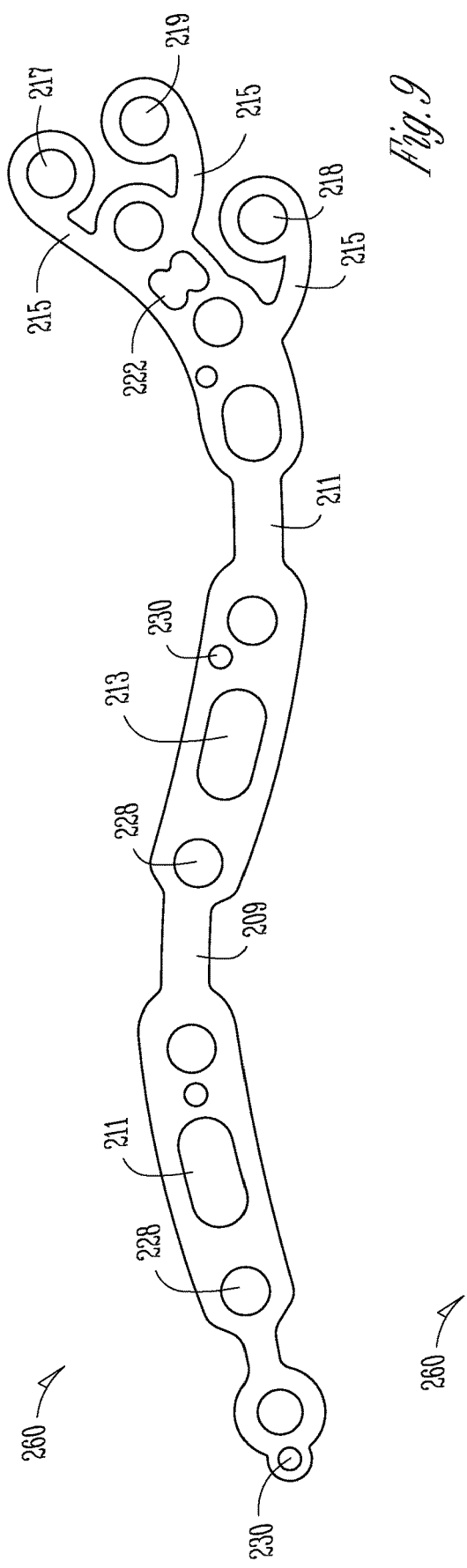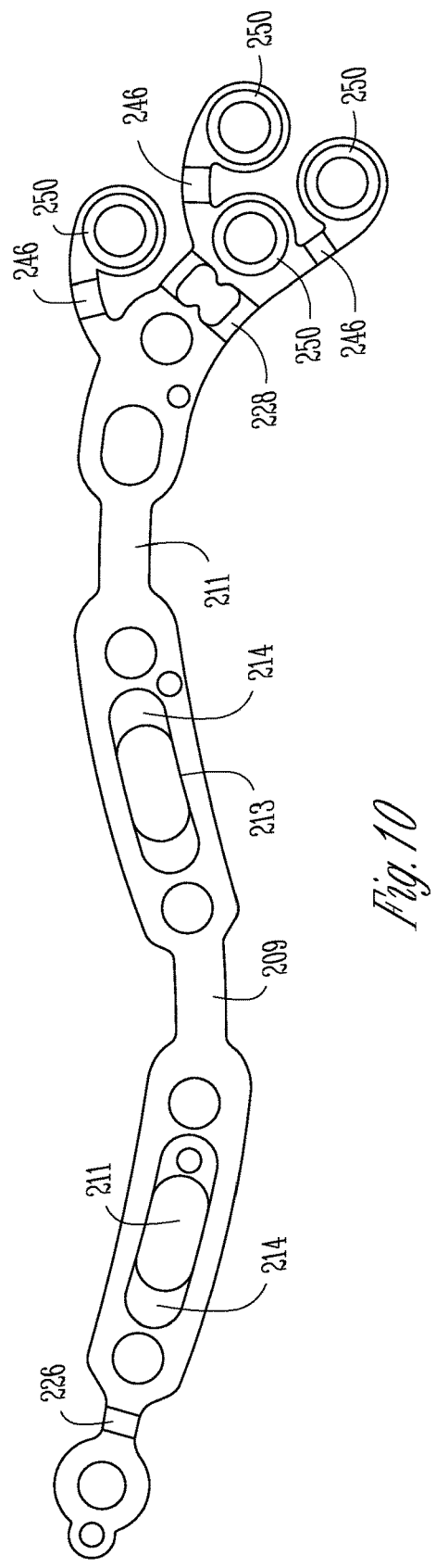

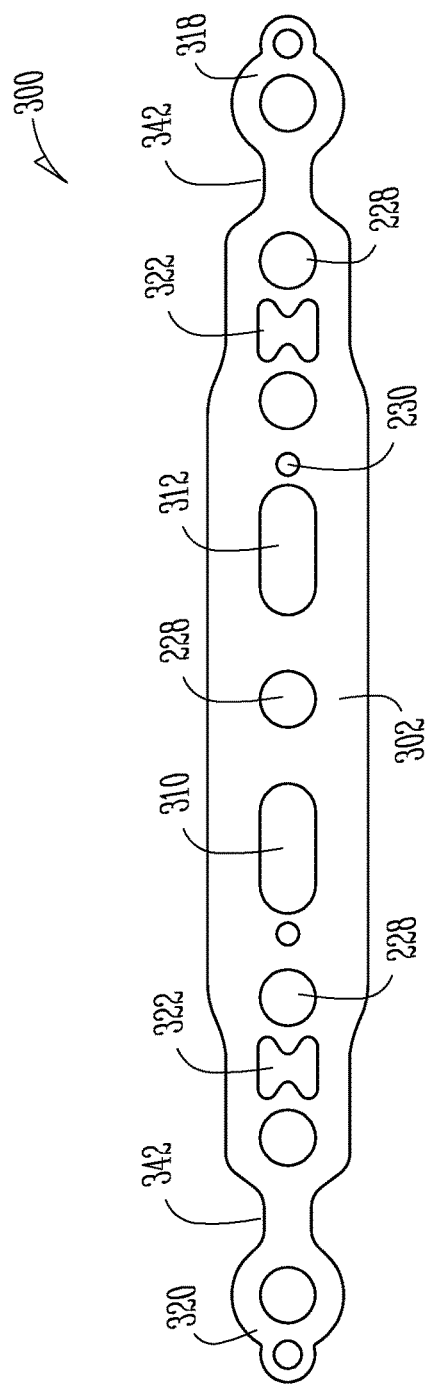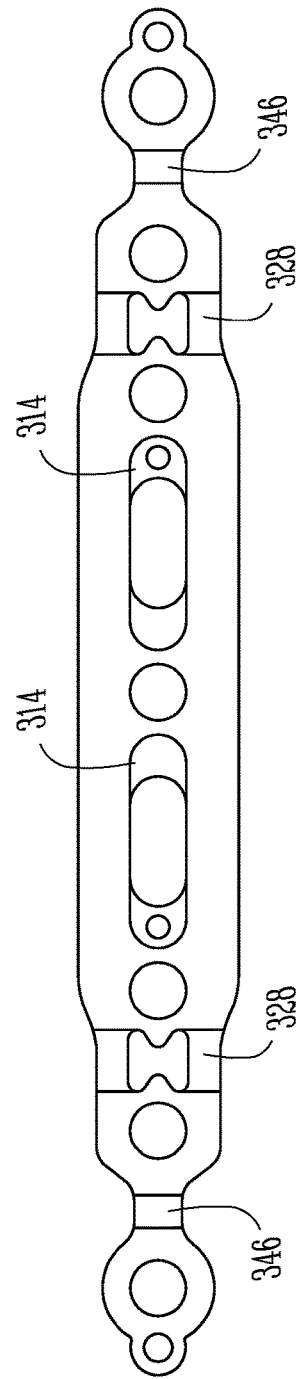

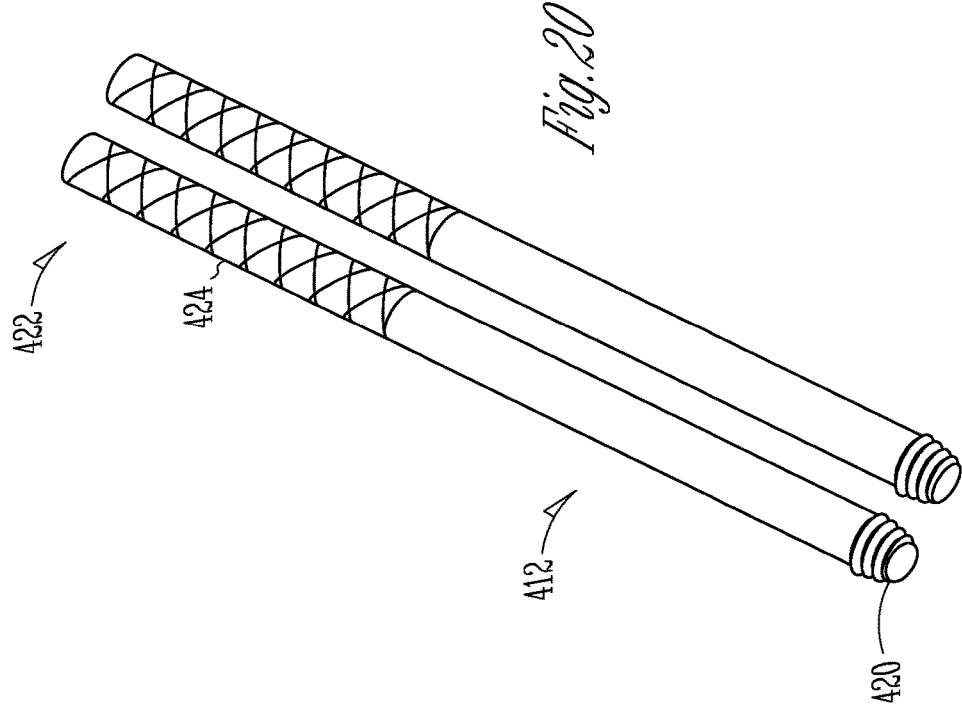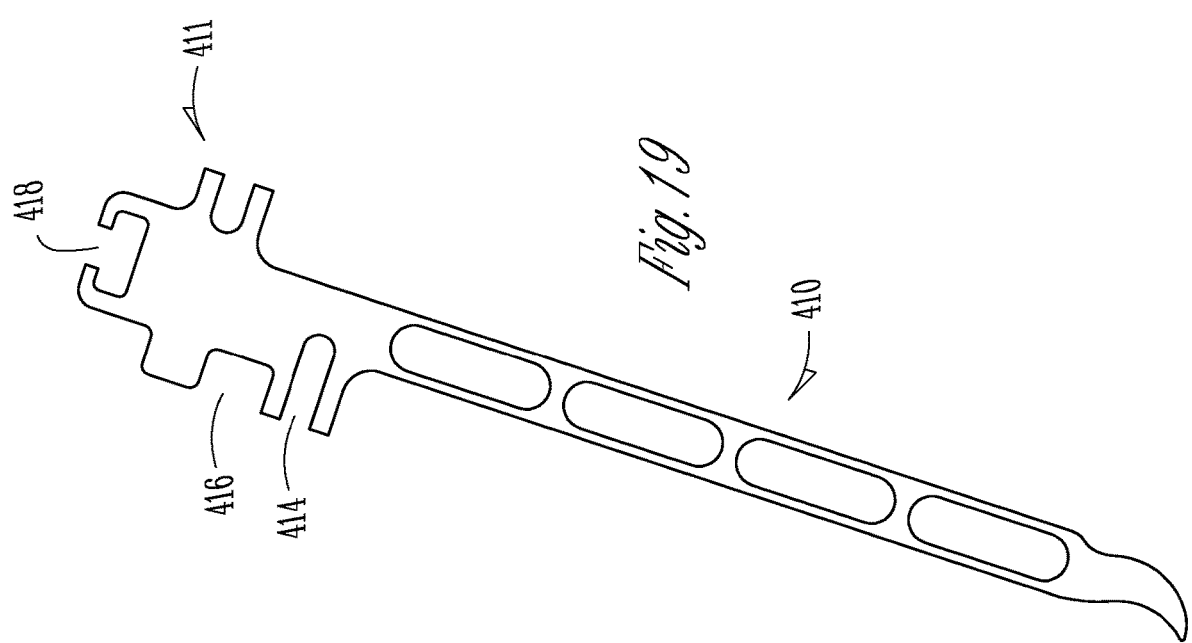

CLAVICLE IMPLANTS

CLAIM OF PRIORITY

This application claims the benefit of priority under 35 U.S.C. § 119(e) of U.S. Provisional Patent Application Ser. No. 62/152,320, filed on Apr. 24, 2015, which is herein incorporated by reference in its entirety.

FIELD

This invention relates broadly to surgery. Particularly, this invention relates to orthopedic devices for fixation of clavicle fractures and methods of using the same.

BACKGROUND

The clavicle is a doubly curved long bone that connects the arm to the trunk of the body. Treatment for fractured clavicles can include placement of a plate and screws or other fasteners on the clavicle.

However, the shape of the clavicle varies more than most other long bones. Specific implants made to address each possible variation would lead to an excessive number of shapes for the plates.

OVERVIEW

In a first example, a bone plate includes a main bone plate body having two opposing curved sections adapted for a clavicle; a bendable waist portion narrower than the main body of the bone plate; and a node at each end of the main body; wherein the main body includes one or more slots, one or more of the slots have a cut-out region on a bottom surface of the bone plate configured to receive a bending iron.

In Example 2, the first Example can optionally include wherein each node is connected to the main body by a bridge portion which is narrower than the main body, wherein the bridge includes a cut-out relief portion on a bottom side of the bone plate.

In Example 3, the bone plate of Example 1 can optionally include wherein the main body includes one or more bone-shaped holes.

In Example 4, the bone plate of Example 3 can optionally include wherein the one or more bone-shaped holes have a cut-out relief portion on a bottom side of the bone plate.

In Example 5, the bone plate of Example 1 can optionally include wherein the bone plate is configured for a superior implant on the clavicle and each of the opposing curved sections defines a radius, with one radius in the range of 60 mm to 90 mm and the other radius in the range 83 mm to 100 mm.

In Example 6, the bone plate of Example 5, can optionally include wherein the waist portion is located between the two curved sections.

In Example 7, the bone plate of Example 1 can optionally include a plurality of holes in the main body configured to receive fasteners.

In Example 8, the bone plate of Example 1 can optionally include wherein the bone plate is configured for a distal implant on the clavicle.

In Example 9, the bone plate of Example 8 can optionally include wherein an end of the bone plate includes a plurality of nodes connected to the main body by bendable bridges.

In Example 10 a system can include a plurality of superior implant bone plates ranging in size from small, medium, and large; each superior implant bone plate including a main bone plate body having two opposing curved sections adapted for a superior surface of a clavicle; a bendable waist portion narrower than the main body of the superior implant bone plate; and a node at each end of the main body; wherein the plurality of superior implant bone plates are configured and bendable so as to fit a range of clavicle radii of 39 mm to 130 mm.

In Example 11 the system of Example 10 can optionally include wherein each of the opposing curved sections of the plurality of superior implant bone plates defines a radius, with one radius in the range of 60 mm to 90 mm and the other radius in the range 83 mm to 100 mm.

In Example 12, the system of Example 10 can optionally include wherein each node is connected to the main body by a bendable bridge portion which is narrower than the main body, and wherein the bendable bridge portion includes a cut-out relief portion on a bottom side of the superior implant bone plate.

In Example 13, the system of Example 10 can optionally include two or more distal implant bone plates configured for a distal implant on the clavicle, each distal implant bone plate including a bendable waist.

In Example 14, the system of Example 13 can optionally include wherein an end of the distal implant bone plates include a plurality of nodes connected to a distal implant main body main body by bendable bridges, wherein each of the nodes include a conical surface on a bottom surface of the distal implant bone plate.

In Example 15, the system of Example 13 can optionally include one or more anterior/inferior implant bone plates.

In Example 16, the system of Example 15 can optionally include wherein each anterior/inferior implant bone plate includes a node at each end of a main body of the anterior/inferior implant bone plate, each node connected to the main body by a bridge.

In Example 17, the system of Example 16 can optionally include a bending iron configured to bend and shape the superior implant bone plates, the distal implant bone plates, and the one or more anterior/inferior implant bone plates; a modifying stick configured to bend and shape the superior implant bone plates, the distal implant bone plates, and the one or more anterior/inferior implant bone plates; and a plurality of fasteners; wherein each of the superior implant bone plates, the distal implant bone plates, and the one or more anterior/inferior implant bone plates, the bending iron, the modifying stick, and the fasteners are located in a sterile container.

Example 18 includes a method comprising providing a plurality superior implant bone plates ranging in size from small, medium, and large; each superior implant bone plate including a main bone plate body having two opposing curved sections adapted for a superior surface of a clavicle; a bendable waist portion narrower than the main body of the superior implant bone plate; and wherein the plurality of superior implant bone plates are configured to fit range of clavicle radii of 39 mm to 130 mm bone plates ranging in size from small, medium, and large; choosing one of the superior implant bone plates depending on the size and shape of the clavicle; and bending the chosen superior implant bone plate at the waist portion to shape the superior implant bone plate to be received on the superior surface of the clavicle.

In Example 19, the method of Example 18 can optionally include wherein the main body includes one or more slots, one or more of the slots have a cut-out region on a bottom surface of the bone plate configured to receive a bending iron In Example 20, the method of Example 18 can optionally include wherein each superior implant bone plate includes a node at each end of the main body connected to the main body by a bendable bridge portion which is narrower than the main body; and the bridge portion includes a cut-out relief portion on a bottom side of the bone plate.

These examples can be combined in any permutation or combination. This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 3 shows a shows a top view of a bone plate, in accordance with one embodiment.

FIG. 4 shows a bottom view of the bone plate of FIG. 3, in accordance with one embodiment.

FIG. 7 shows a shows a top view of a bone plate, in accordance with one embodiment.

FIG. 8 shows a bottom view of the bone plate of FIG. 7, in accordance with one embodiment.

FIG. 9 shows a shows a top view of a bone plate, in accordance with one embodiment.

FIG. 10 shows a bottom view of the bone plate of FIG. 9, in accordance with one embodiment.

FIG. 11 shows a shows a top view of a bone plate, in accordance with one embodiment.

FIG. 12 shows a bottom view of the bone plate of FIG. 11, in accordance with one embodiment.

FIG. 19 shows a perspective view of a bending iron, in accordance with one embodiment.

FIG. 20 shows a modifying stick, in accordance with one embodiment.

DETAILED DESCRIPTION

Figure 1:
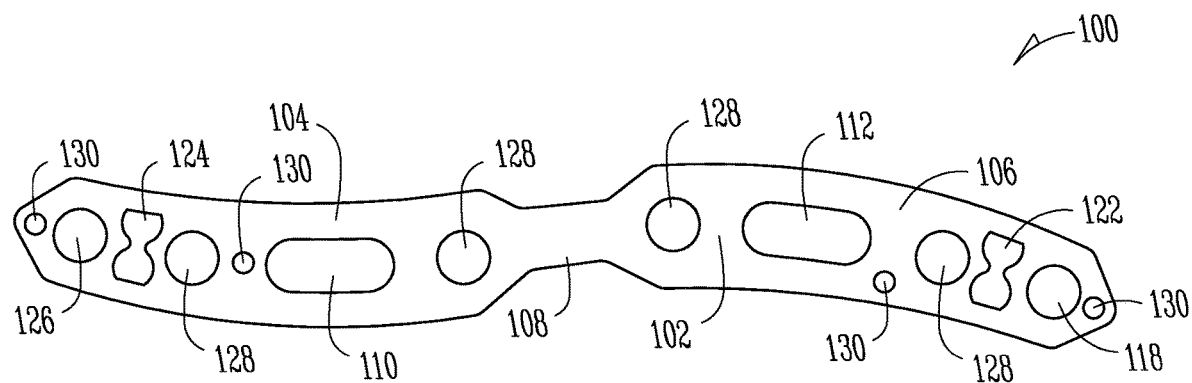
FIG. 1 shows a shows a top view of a bone plate, in accordance with one embodiment.
Figure 2:
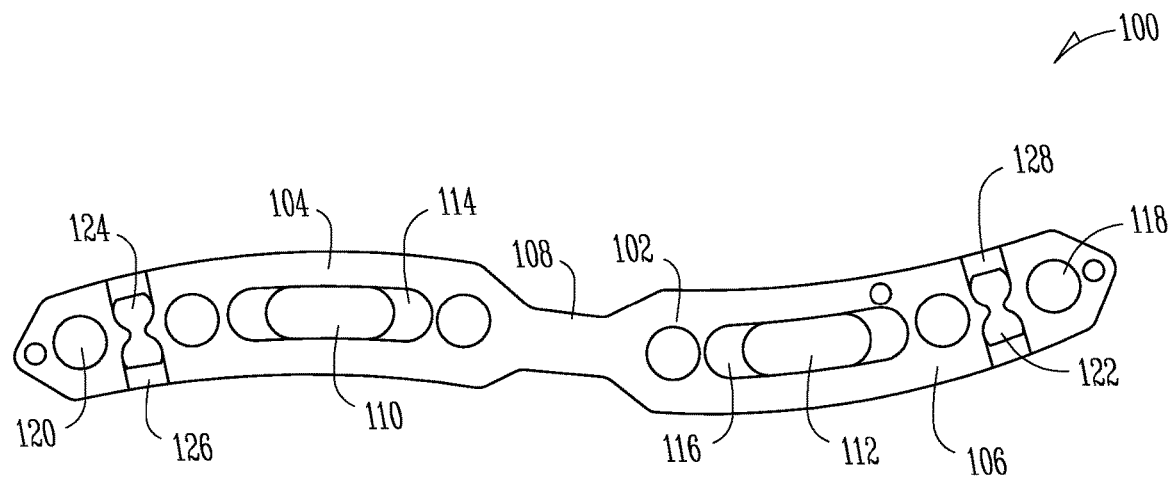
FIG. 2 shows a bottom view of the bone plate of FIG. 1, in accordance with one embodiment.

FIG. 1 shows a shows a top view of a bone plate 100, in accordance with one embodiment; and FIG. 2 shows a bottom view of the bone plate 100. Bone plate 100 can include a main bone plate body 102 having two opposing curved sections 104, 106 adapted for a superior surface of a clavicle. A bendable waist portion 108 narrower than the main body 102 of the bone plate 100 can be located between the two curved sections 104 and 106.

The main body can include one or more slots 110, 112. The slots 110 and 112 can include a cut-out region 114, 116 on a bottom surface of the bone plate 100 under the slots 110, 112. The slots 110 and 112 with the cut-out regions 114, 116 are configured to receive a bending iron. This allows a user to bend a chosen bone plate 100 to a desired shape depending on the clavicle being repaired. The bending can take place at the bendable waist 108, for example. Also, allowing to contour the plate 100 in a concave and convex direction. Also, cut-out region 114, 116 can define a relief region help to reduce any damage to the periosteum on the clavicle.

The bone plate 100 can include a node 118, 120 at each end of the main body 102. The nodes 118 and 120 can be sized to receive a modifying stick or bending iron which allows for further bending and shaping of the bone plate 100.

The bone plate 100 can include one or more bone-shaped holes 122, 124 proximate the ends of the bone plate 100. The bone-shaped holes also help for shaping the bone plate 100 while not compromising the torsional strength of the bone plate 100. The bone-shaped holes 122, 124 can have a cut-out relief portion 126, 128 on a bottom side of the bone plate 100. The relief portions 126, 128 can help to reduce any damage to the periosteum on the clavicle. Past bone plates often require significant soft tissue stripping, which may compromise blood supply to the bone and subsequent healing.

Bone plate 110 can include a plurality of holes in the main body 102 configured to receive fasteners. For example, the bone plate can include screw holes 128 and K-wire holes 130. These, along with the nodes 118, 120 and the dog-bone shaped holes 122, 124 can receive screws, sutures, or other fasteners to mount the bone plate 100 to the clavicle.

FIG. 3 shows a shows a top view of a bone plate 140, in accordance with one embodiment; and FIG. 4 shows a bottom view of the bone plate 140.

Bone plate 140 includes many similar features as bone plate 100 and like numbering is used and certain details will not be discussed and can be incorporated from the discussion of bone plate 100 above.

Bone plate 140 can include the node 118, 120 at each end of a main body 141 connected to the main body 141 by a bendable bridge portion 142, 144 which is narrower than the main body 141. This bridge portion 142, 144 allows for bending, or if desired one or both nodes 118, 120 can be torn of the main body 141 at the bridge portions 142, 144. The bridge portions 142, 144 can include a cut-out relief portion 146, 148 on a bottom side of the bone plate 140. Again, the relief portions 146, 148 help to reduce any damage to the periosteum on the clavicle.

Figure 5:
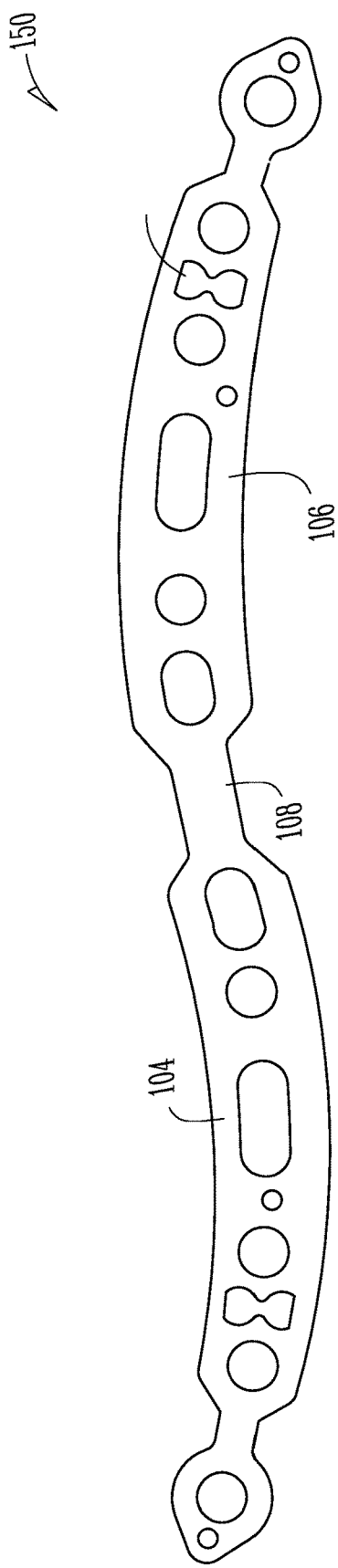
FIG. 5 shows a shows a top view of a bone plate, in accordance with one embodiment.
Figure 6:
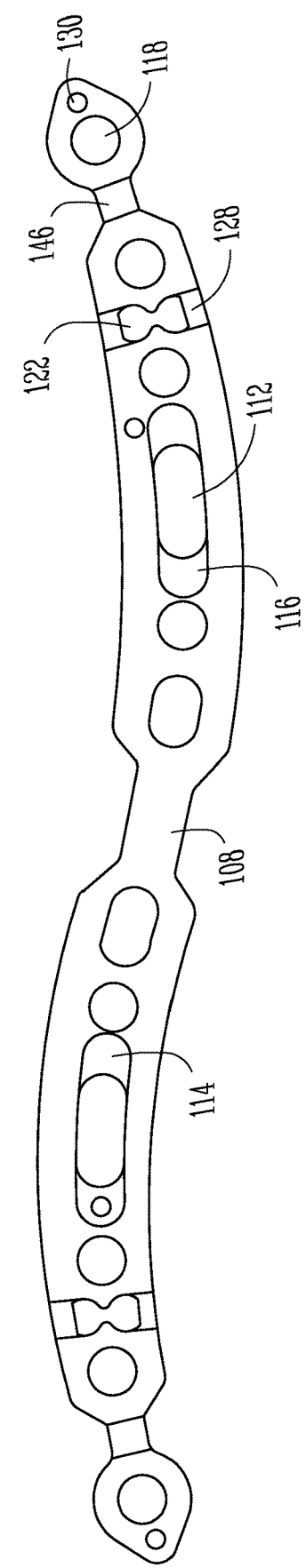
FIG. 6 shows a bottom view of the bone plate of FIG. 5, in accordance with one embodiment.
Figure 13:
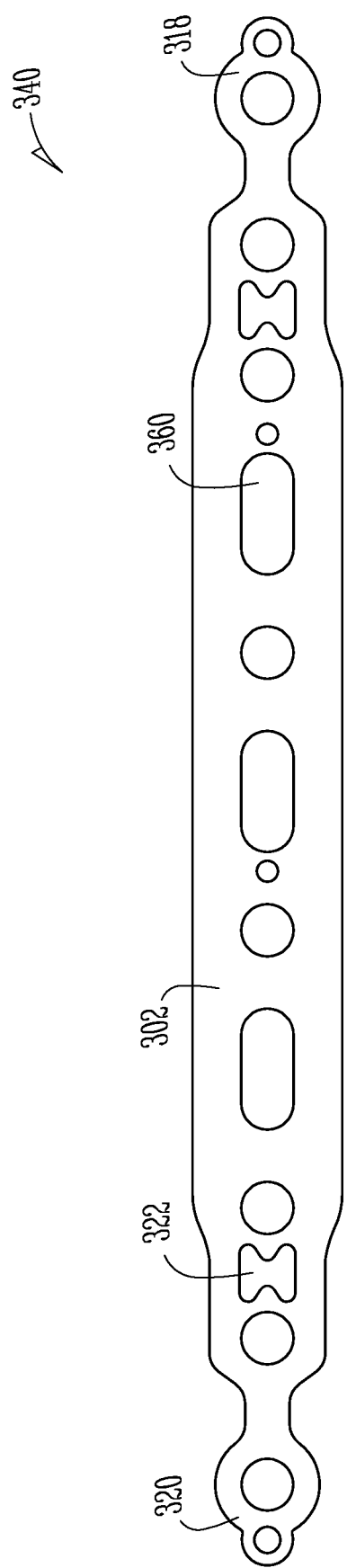
FIG. 13 shows a shows a top view of a bone plate, in accordance with one embodiment.
Figure 14:
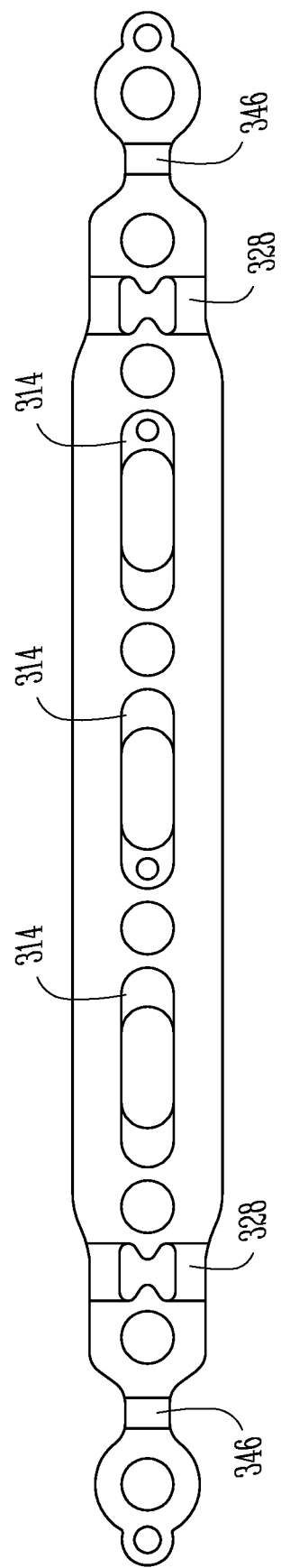
FIG. 14 shows a bottom view of the bone plate of FIG. 13, in accordance with one embodiment.
Figure 15:
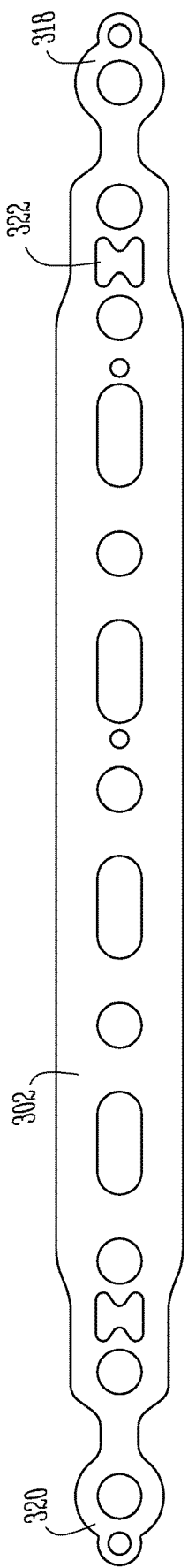
FIG. 15 shows a shows a top view of a bone plate, in accordance with one embodiment.
Figure 16:
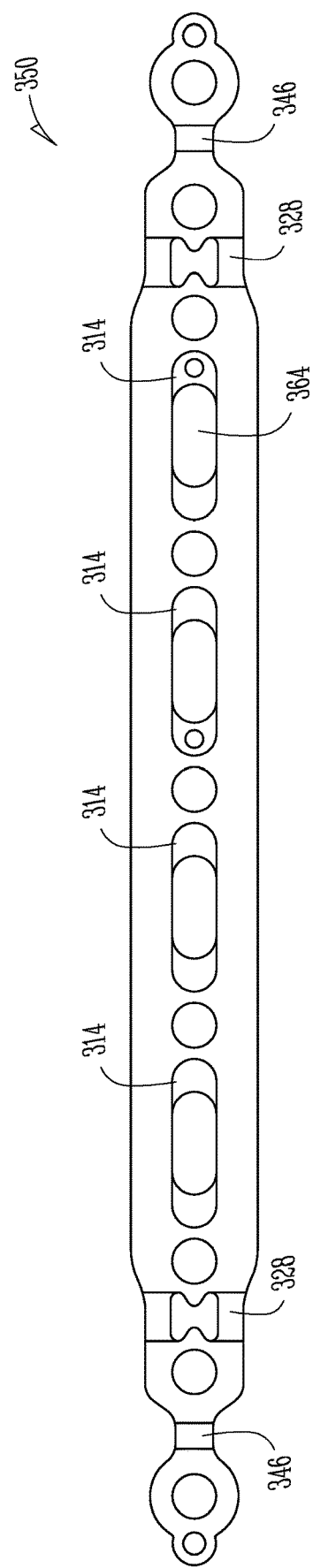
FIG. 16 shows a bottom view of the bone plate of FIG. 15, in accordance with one embodiment.

FIG. 5 shows a shows a top view of a bone plate 150, in accordance with one embodiment; and FIG. 6 shows a bottom view of the bone plate 150.

Bone plate 150 includes many similar features as bone plates 100 and 104 and like numbering is used and certain details will not be discussed and can be incorporated from the discussion of bone plates 100 and 104 above.

Referring to FIGS. 1-6, the bone plates, 100, 140, and 150 differ in size and geometry. In an example, they can be used in a kit of parts and are configured as a group to cover a majority of clavicle injuries requiring superior implant bone plates.

| Clavicles by length | Bone length range | Large radius range | Large radius average | Small radius range | Small radius average |
|---|---|---|---|---|---|
| Full Range | 114 mm-171 mm | 72 mm-130 mm | 98 mm | 39 mm-110 mm | 71 mm |
| Shortest (30%) | 114 mm-133 mm | 78 mm-8S mm | 83 mm | 40 mm-52 mm | 47 mm |
| Middle 30% | 134 mm-152 mm | 72 mm-130 mm | 97 mm | 39 mm-100 mm | 72 mm |
| Longest 30% | 153 mm-171 mm | 80 mm-110 mm | 102 mm | 45 mm-110 mm | 76 mm |

The Table above show ranges of clavicle features taken from a library of 30 clavicle bones. Three bones were considered "Shortest". Fourteen bones were in the "Middle", and thirteen represented the expected "Longest". The range of features such as Bone Length and the Large Radius and Small Radius were studied. The objective was to provide a small number of implants that could be installed on all 30 of the clavicles in the bone library.

What resulted was a bone plate design that could be placed in two orientations due to the fact that in some instances the lateral curvature is larger than the medial curvature of the clavicle, and sometimes it is the opposite. Historically, 80% of fractures occur in the middle of the clavicle.

The present bone plates 100, 140, 150 can be configured with the bending waist 108 to be placed near the inflection point of the clavicle anatomy at the area between the two radius features of the clavicle.

Referring to the table below, example geometries of the bone plates 100, 140, and 150 are shown. The curvatures of the implant plates were selected to cover the range of anatomical variation from the table above. The radii selected covers the full range of large and small clavicle radii from the above table, a range from 39 mm to 130 mm. In an example, three sets of radiuses combined with the waist bending feature of the plates can allow them to properly fit a significant portion of the anatomical variation expected. The mirror image of the plates can be made for the opposing side of the clavicle, and with as little as six implants a set or kit of implant plates that will cover 80% of the typical fractures of the clavicle can be provided.

| Plate | Length | Large Radius | Small radius |
|---|---|---|---|
| Small plate (100) | 87 mm | 83 mm | 60 mm |
| Medium plate (140) | 110 mm | 94 mm | 70 mm |
| Large plate (150) | 122 mm | 100 mm | 90 mm |

Thus a system can include a plurality of superior implant bone plates 100, 140, 150 ranging in size from small, medium, and large. Each superior implant bone plates can include a main bone plate body having two opposing curved sections adapted for a superior surface of a clavicle. Each bone plate 100, 140, 150 can include the bendable waist portion 108 and a node 118, 120 at each end of the main body connected to the main body, wherein the plurality of superior implant bone plates are configured to fit range of clavicle radii of 39 mm to 130 mm. In an example, bone plates 100, 140, 160 can include one or more slots, one or more of the slots having a cut-out region 114, 116 on a bottom surface of the bone plate configured to receive a bending iron.

In an example, each of the opposing curved sections 104, 106 of the bone plates 100, 140, 150 can define a radius, with one radius in the range of 60 mm to 90 mm and the other radius in the range 83 mm to 100 mm.

FIG. 7 shows a shows a top view of a bone plate 200, in accordance with one embodiment; and FIG. 8 shows a bottom view of the bone plate 200. In an example, bone plate 200 can be configured for a distal implant on the clavicle.

Bone plate 200 includes many similarities to the features of bone plates 100, 140, and 150 discussed above. Similar to the superior bone plates 100, 140, 150, the distal bone plate 200 can have the same radius and waist features to ensure proper fit. For example, bone plate 200 can include a main body 202 having a radius and curvature and having a bendable waist 208. A slot 210 can have a cut-out region 214 on a bottom surface of the bone plate 200 configured to receive a bending iron to shape the plate 200 to a desired curvature. The bone plate can include one or more bone-shaped holes 222. Each of the bone-shaped holes 222 can have a cut-out relief portion 228 on a bottom side of the bone plate 200. Bone plate 200 can include a plurality of holes to receive fasteners, such as holes 228 and K-wire holes 230.

Here, the bone plate can include a node 220 on one end connected by a bendable bridge 244. The bendable bridge 244 can include a cut-out relief portion 226 on a bottom side of the bone plate. On the other end of the bone plate 200, the bone plate 200 can include a node 221 and plurality of nodes 217, 218, 219 connected to the main body by bendable bridges 215, forming a fiddlehead shaped feature. Bridges 215 can include a cut-out relief portion 246 on a bottom side of the bone plate. The nodes 217, 218, 219 forming the fiddlehead feature allows a physician to better match the top surface of the clavicle by bending and shaping the bone plate 200.

Moreover, the nodes 217, 218, 219 can be bent and shaped around the surface of the clavicle such that they result in assuring that the screw trajectories are not all in the same direction. This helps because the failure mode of current distal implants can happen when the screws are pulled out in tension. The fiddlehead feature makes it likely that the loading characteristics are in shear as the screws are inserted at different angles. In some options, one or more of the nodes 217, 218, 219 are not necessary or the anatomy is narrow making it more desirable to have less nodes. In these instances one or more nodes 217, 218, 219 can be torn off the main body 202 to customize the implant plate. In one example the bottom sides of sides of one or more of the nodes 217, 218, 219, 220, 221 can include a concave or conical relief portion 250 in order to minimize the periosteum that can be damaged by the implant.

FIG. 9 shows a shows a top view of a bone plate 260, in accordance with one embodiment; and FIG. 10 shows a bottom view of the bone plate 260.

Bone plate 260 is also configured for distal clavicle use and can include many similar features as bone plate 200 and like numbering is used and certain details will not be discussed and can be incorporated from the discussion of bone plate 200 above.

Here bone plate 260 is larger than bone plate 200 and can include two opposing curved sections, one or more bendable waist sections 209, 211, and first and second slots 211, 213. Each slot 211, 213 can include a cut-out region 214 on a bottom surface of the bone plate 260 configured to receive a bending iron to shape the plate 260 to a desired curvature.

In both bone plates 200, 260 the placement of the bendable waists 208, 209, 211 can coincide with locations were the clavicle curvature typically has inflection points where the curvature changes.

Another part of a clavicle system can include anterior/inferior bone plates. FIGS. 11-16 show various sizes of anterior/inferior bone plates 300, 340, 350. The anterior/inferior implant plates can have similar features to the other bone plates discussed above. For example, the bone plates 300, 340, 350 can include an elongate main body 302 having one or more slots 310, 312, 360, 364. The slots, 310, 312, 360, 364 can have a cut-out region 314 on a bottom surface of the bone plate configured to receive a bending iron to shape the plate 300, 340, 350 to a desired curvature. This allows a physician a starting point to impart the secondary bends that are unpredictable dependent on anatomical differences.

The bone plate can include one or more bone-shaped holes 322. Each of the bone-shaped holes 322 can have a cut-out relief portion 328 on a bottom side of the bone plate. Bone plates 200 can also include a plurality of holes to receive fasteners, such as holes 228 and K-wire holes 230.

Bone plates 300, 340, 350 can include a node 318, 320 at each end of a main body 302 and connected to the main body 302 by a bendable bridge portion 342, As discussed for the previous bone plates, the bridge portion 342 allows for bending, or if desired one or both nodes 318, 320 can be torn of the main body 302 at the bridge portions 342. The bridge portions 342 can include a cut-out relief portion 346 on a bottom side of the bone plate. Again, the relief portions 346 and the other relief portions discussed on the plates herein help to reduce any damage to the periosteum on the clavicle.

Figure 17:
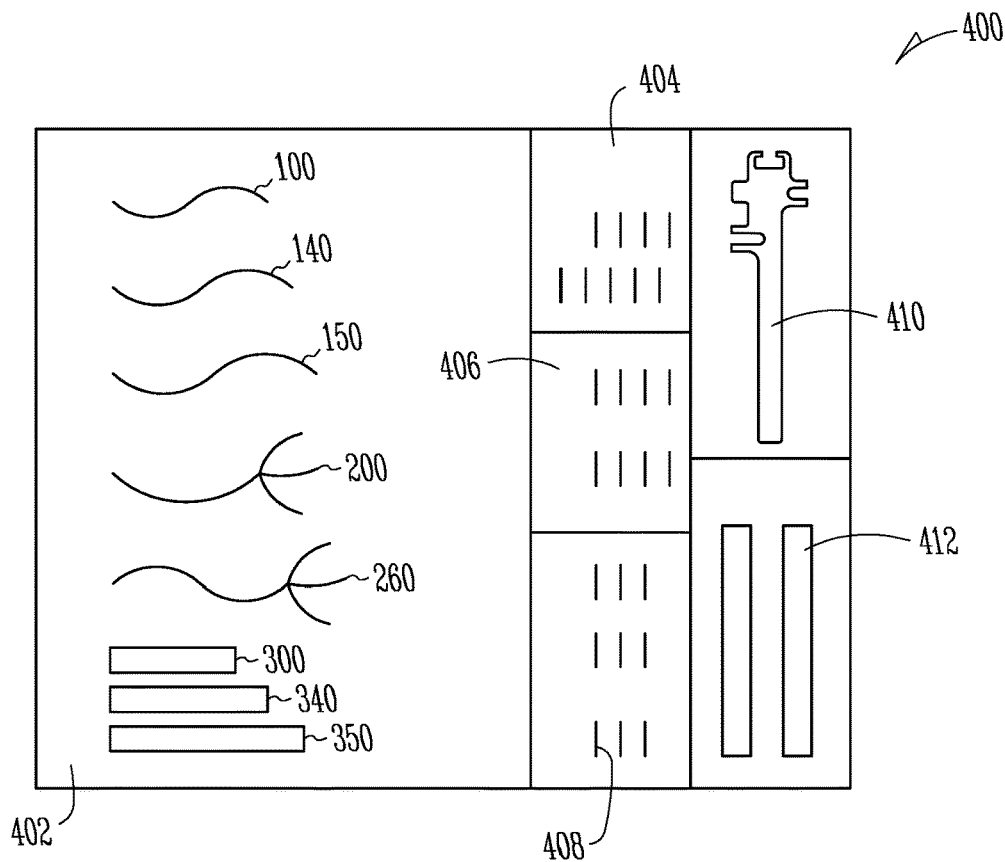
FIG. 17 shows a schematic of a kit for clavicle repair, in accordance with one embodiment.

FIG. 17 shows a schematic of a kit 400 for clavicle repair, in accordance with one embodiment. A system of providing bone plates discussed above can include a kit 400. The kit can include an autoclavable sterilized container 402 including a lid (not shown). There can be supplied one or more bone plates discussed above. For example, kit 400 can include bone plates 100, 140, 150, 200, 260, 300, 340, and 340. In one option, the mirror image of the bone plates 100, 140, 150 can be added to be used the opposing side of the clavicle. In other options, more or fewer bone plates can be added or removed.

The kit 400 can further include one or more of locking screws 404, non-locking screws 406, and variable angle locking screws 408. An option for a single fastener for the bone plates discussed herein is the variable angle locking screw 406 which can lock in the direction of the thread, can be locked off axis, and with little modifications could be inserted into a slot to act as a non-locking screw. In an option, the kit 400 can also be segregated by screw size. Regardless, of if they are superior, distal, or anterior/inferior plates, they can either function with 3.5 mm screws or 2.7 mm screws.

Figure 18:
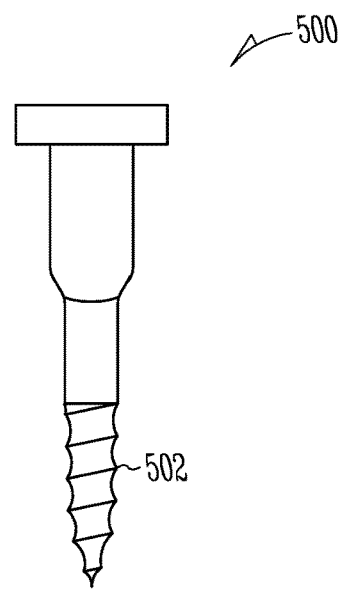
FIG. 18 shows a side view of a screw, in accordance with one embodiment.

One option for a fastener screw is shown in FIG. 18. FIG. 18 shows a side view of a screw 500, in accordance with one embodiment. Screw 500 is a variable angle screw and can be made of titanium molybdenum. This titanium alloy is useful because it can be heat treated to increase the hardness. The screw 500 can include a self-drilling and tapping tip 502. This prevents the physician from drilling through the far cortex which could be dangerous as various arteries, veins, and plexus of nerves are present within millimeters of the clavicle. Using screw 500, the physician can drill through the near cortex with a drill. Then the physician can use the drill or a depth gauge to understand the depth to the far cortex, and then add 1 or 2 mm to account for the far cortex to select the appropriate sized self-drilling and tapping screw 500.

Referring again to FIG. 17, the kit 400 can further include a bending iron 410 configured to bend and shape the superior implant bone plates 100, 140, 150, the distal implant bone plates 200, 260, and the one or more anterior/inferior implant bone plates 300, 340, 350. The kit 400 can also include one or more modifying sticks 412. The modifying stick 412 are configured to bend and shape the superior implant bone plates, the distal implant bone plates, and the one or more anterior/inferior implant bone plates;

FIG. 19 shows a perspective view of one option for the bending iron 410, in accordance with one embodiment. The bending iron 410 is able to contour plates in various directions using various bending and gripping features 411, 414, 416, and 418. This gives a greater freedom allowing combinations of concave or convex with a twist. One or more of features 411, 414, 416, and 418 can be used to bend plates using either the slots on the plates or the nodes on the plates.

FIG. 20 shows one option for the modifying stick 412, in accordance with one embodiment.

The modifying stick 412 can be configured to bend and shape the superior implant bone plates, the distal implant bone plates, and the one or more anterior/inferior implant bone plates. The nodes on the ends of the implant plates can allow customization with the sticks 412 and can be tom off to modify the length of the implant. This feature further enhances the ability of the set of implant plates to fit a wider range of anatomical variation. The sticks 412 can modify the implant at the nodes and also at the bone shaped features at either end of the implant.

Moreover, the sticks 412 can serve as drill guides, implant plant handles, and drill safety stops. The sticks 412 can include a threaded end 420, and driver features on the other end 422. Knurls 424 can be provided to aid as a grip feature.

In use of a system according to the above discussion a kit can be provided having a plurality superior implant bone plates ranging in size from small, medium, and large; each superior implant bone plate including a main bone plate body having two opposing curved sections adapted for a superior surface of a clavicle; a bendable waist portion narrower than the main body of the superior implant bone plate; and the plurality of superior implant bone plates are configured to fit range of clavicle radii of 39 mm to 130 mm bone plates ranging in size from small, medium, and large. A user chooses one of the superior implant bone plates depending on the size and shape of the clavicle, and then can bend the chosen superior implant bone plate at the waist portion to shape the superior implant bone plate to be received on the superior surface of the clavicle.

As discussed, distal implant plates and anterior/inferior plates can also be provided, and used as needed. In both the superior and distal implants discussed above, the k-wire holes 230 have been designed to accept sutures. This allows tethering to the coracoid. An option is to use the implant in conjunction with a fixation device. A physician can deploy the fixation device directly into the coracoid, and then tether the suture directly to the implant. The attachment points can also include the bone shaped features and the bridges that connect to the nodes. This allows triangulation, which aids in the unloading of the distal screws which tend to fail because the distal cortex is often very thin.

The plates and systems discussed herein offer superior clavicle bone plates and distal clavicle bone plates that use a range of radiuses. In combination with a bendable waist feature to ensure fit. This provides for a system where relatively few plates are needed to cover a majority of clavicle fractures. Also, the plates come with features with features that ensure minimum compression of the periosteum ensuring that vascular connection between connective tissue and bone is minimally disrupted.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The claimed invention is:

1. A bone plate comprising:
a main bone plate body having an S-shape defining two opposing curved sections adapted for a clavicle;
a bendable waist portion narrower than the main body of the bone plate and located between the two opposing curved sections; and
a first node and a second node, with the first node at the end of one of the two opposing curved sections and the second node at the end of the other of the two opposing curved sections;
wherein the main body includes a bone-facing bottom surface positioned against the bone when implanted and an opposite, upper surface facing away from the bone when implanted, and wherein the main body includes one or more slots extending all the way through the main bone plate body from the bone-facing bottom surface to the opposite, upper surface, one or more of the slots have a cut-out region on the bottom surface of the bone plate at a periphery of the slot, the slot being configured to receive a bending iron positioned within the slot.

2. The bone plate of claim 1, wherein each node is connected to the end of one of the two opposing curved sections of the main body by a bridge portion which is narrower than the main body, wherein the bridge includes a cut-out relief portion on a bottom side of the bone plate.

3. The bone plate of claim 1, wherein the main body includes one or more bone-shaped holes.

4. The bone plate of claim 3, wherein the one or more bone-shaped holes have a cut-out relief portion on a bottom side of the bone plate.

5. The bone plate of claim 1 wherein the bone plate is configured for a superior implant on the clavicle and each of the opposing curved sections defines a radius, with one radius in the range of 60 mm to 90 mm and the other radius in the range 83 mm to 100 mm.

6. The bone plate of claim 5, wherein the waist portion is located between the two curved sections.

7. The bone plate of claim 1, further including a plurality of holes in the main body configured to receive fasteners.

8. The bone plate of claim 1, wherein the bone plate is configured for distal clavicle implant.

9. The bone plate of claim 8, wherein an end of the bone plate includes a plurality of additional nodes connected to the main body by bendable bridges.

10. A system comprising:
three superior implant bone plates ranging in size of a small size, a medium size, and a large size;
each superior implant bone plate including a main bone plate body having an S-shape defining two opposing curved sections adapted for a superior surface of a clavicle wherein each of the opposing curved sections defines a radius with the one radius of the three bones plates ranging from 60 mm to 90 mm and the other radius of the three bone plates ranging from 83 mm to 100 mm;
a bendable waist portion narrower than the main body of the superior implant bone plate and located between the two opposing curved sections; and
a first node and a second node, with the first node at the end of one of the two opposing curved sections and the second noted at the end of the other of the two opposing curved sections;
wherein the three superior implant bone plates are configured and bendable so as to fit a range of clavicle radii of 39 mm to 130 mm.

11. The system of claim 10, wherein each node is connected to the end of one of the two opposing curved sections of the main body by a bendable bridge portion which is narrower than the main body, and wherein the bendable bridge portion includes a cut-out relief portion on a bottom side of the superior implant bone plate.

12. The system of claim 10 further including two or more distal implant bone plates configured for a distal clavicle implant, each distal implant bone plate including a bendable waist.

13. The system of claim 12, wherein an end of the distal implant bone plates include a plurality of additional nodes connected to a distal implant main body main body by bendable bridges, wherein each of the nodes include a conical surface on a bottom surface of the distal implant bone plates.

14. The system of claim 12, further including one or more anterior/inferior implant bone plates, the one or more anterior/inferior implant bone plates being relatively straight compared to the distal implant bone plates.

15. The system of claim 14, wherein each anterior/inferior implant bone plate includes an additional node at each end of a main body of the anterior/inferior implant bone plate, each additional node connected to the main body by a bridge.

16. The system of claim 15, further including a bending iron configured to bend and shape the superior implant bone plates, the distal implant bone plates, and the one or more anterior/inferior implant bone plates; a modifying stick configured to bend and shape the superior implant bone plates by being inserted into a node of the bone plate, the distal implant bone plates, and the one or more anterior/inferior implant bone plates; and a plurality of fasteners configured to be received by a plurality of holes on the bone plate; wherein each of the superior implant bone plates, the distal implant bone plates, and the one or more anterior/inferior implant bone plates, the bending iron, the modifying stick, and the fasteners are located in a sterile container.

* * * * *